(12) United States Patent
Ishikawa et al.

(10) Patent No.: US 9,340,002 B2
(45) Date of Patent: May 17, 2016

(54) METHOD OF MANUFACTURING WET WIPES, MANUFACTURING APPARATUS, AND WET WIPES

(75) Inventors: Yoshihide Ishikawa, Kagawa (JP); Takeshi Bando, Kagawa (JP)

(73) Assignee: UNICHARM CORPORATION, Ehime-Ken (JP)

( * ) Notice: Subject to any disclaimer, the term of this patent is extended or adjusted under 35 U.S.C. 154(b) by 549 days.

(21) Appl. No.: 13/640,331

(22) PCT Filed: Apr. 12, 2011

(86) PCT No.: PCT/JP2011/059088
§ 371 (c)(1),
(2), (4) Date: Nov. 26, 2012

(87) PCT Pub. No.: WO2011/129330
PCT Pub. Date: Oct. 20, 2011

(65) Prior Publication Data
US 2013/0061410 A1    Mar. 14, 2013

(30) Foreign Application Priority Data
Apr. 12, 2010   (JP) ................................. 2010-091724

(51) Int. Cl.
*B32B 38/08*      (2006.01)
*B32B 5/02*      (2006.01)
(Continued)

(52) U.S. Cl.
CPC ................. *B32B 38/08* (2013.01); *A47K 10/16* (2013.01); *A61K 8/0208* (2013.01); *B32B 5/022* (2013.01); *B32B 29/02* (2013.01); *B65D 83/08* (2013.01); *B65H 45/20* (2013.01); *B65H 45/24* (2013.01); *A47K 2010/3266* (2013.01); *A47K 2010/428* (2013.01); *B32B 2555/00* (2013.01); *Y10T 156/1051* (2015.01)

(58) Field of Classification Search
CPC .......... A47K 7/00; B65D 83/08; B65H 45/20; B65H 45/24; B32B 38/08; B32B 5/022; B32B 29/02
See application file for complete search history.

(56) References Cited

U.S. PATENT DOCUMENTS 3,199,861 A    8/1965   Presnell et al.
3,330,553 A *   7/1967   Couzens et al. ................ 270/40
(Continued)

FOREIGN PATENT DOCUMENTS

JP        7204118 A    8/1995
JP        2777871 B2    7/1998
(Continued)

OTHER PUBLICATIONS

Office Action mailed Feb. 8, 2014, corresponds to Chinese patent application No. 201010166290.9.
(Continued)

*Primary Examiner* — Randall Chin
(74) *Attorney, Agent, or Firm* — Hauptman Ham, LLP (57) ABSTRACT

A method of manufacturing wet wipes includes a step of continuously conveying a plurality of sheets by a conveyor, a step of folding each of the sheets toward a conveyor non-contact surface side of the sheets, a step of impregnating each of the folded sheets with the predetermined chemical solution, from a conveyor contact surface side of the sheets a step of laminating each of the sheets impregnated with the predetermined chemical solution, and a step of cutting the laminated sheets.

6 Claims, 7 Drawing Sheets

(51) Int. Cl.
    *B65H 45/20*     (2006.01)
    *B65H 45/24*     (2006.01)
    *B65D 83/08*     (2006.01)
    *A47K 10/16*     (2006.01)
    *A61K 8/02*     (2006.01)
    *B32B 29/02*     (2006.01)
    *A47K 10/32*     (2006.01)
    *A47K 10/42*     (2006.01)

(56) References Cited

U.S. PATENT DOCUMENTS

| | | | |
|---|---|---|---|
| 6,202,845 | B1 | 3/2001 | Hill |
| 6,213,344 | B1 | 4/2001 | Hill |
| 2003/0125180 | A1* | 7/2003 | Sosalla .................. 493/423 |

FOREIGN PATENT DOCUMENTS

| | | |
|---|---|---|
| JP | 2000512878 A | 10/2000 |
| JP | 2001286410 A | 10/2001 |
| JP | 200338383 A | 2/2003 |
| JP | 2007144053 A | 6/2007 |
| WO | 98/52454 A1 | 11/1998 |

OTHER PUBLICATIONS

International Search Report corresponding to PCT/JP2011/059088, dated May 17, 2011.
Office Action issued May 21, 2014, corresponds to Japanese patent application No. 2010-091724.
Office Action issued Apr. 27, 2015, corresponding to Taiwanese patent application No. 100112663.

* cited by examiner

METHOD OF MANUFACTURING WET WIPES, MANUFACTURING APPARATUS, AND WET WIPES

RELATED APPLICATIONS

The present application is a National Phase of International Application Number PCT/JP2011/059088, filed Apr. 12, 2011, and claims priority from Japanese Application Number 2010-091724, filed Apr. 12, 2010.

TECHNICAL FIELD

The present invention relates to a method of manufacturing wet wipes, a manufacturing apparatus, and wet wipes.

BACKGROUND ART

The methods disclosed in Patent Literature 1 and Patent Literature 2 are known as methods for manufacturing wet wipes including a laminated body of sheets impregnated with a predetermined chemical solution.

The method disclosed in Patent Literature 1 includes a step of impregnating the original fabric sheet, that is being conveyed prior to lamination, with a part of a predetermined chemical solution, a step of wringing out the excess predetermined chemical solution with which the original fabric sheet that is being conveyed is impregnated, a step of laminating a plurality of original fabric sheets that are being conveyed, and a step of impregnating the original fabric sheet, that is being conveyed after lamination, with the remaining predetermined chemical solution.

Furthermore, the method disclosed in Patent Literature 2 includes a step of impregnating the original fabric sheet, that is being conveyed prior to lamination, with a predetermined chemical solution, a step of laminating the original fabric sheet that is being conveyed while folding up the fabric sheet, and a step of cutting the original fabric sheet after lamination, after the fabric sheet has been compressed in the thickness direction and conveyed.

The wet wipes manufactured by the method disclosed in Patent Literature 1 and Patent Literature 2 have a so-called pop-up type in which when a single sheet is taken out from the package, the next sheet is also pulled out together and protrudes out from the slot of the container.

CITATION LIST

Patent Literature

[PTL 1] Japanese Unexamined Patent Application Publication No. H07-204118
[PTL 2] Japanese Unexamined Patent Application Publication No. 2007-144053

SUMMARY OF INVENTION

Problem(s) to be Solved by Invention

However, a problem with the wet wipes having a pop-up type is that when the rate of impregnation of the chemical solution to the original fabric sheet is increased, the original fabric sheets get joined by the water film of the chemical solution, and it make it difficult to take out one sheet from the package, and as a result the rate of the chemical solution to the original fabric sheet is to be controlled at a relatively low value.

Furthermore, according to the method disclosed in Patent Literature 1, because it is necessary to perform the process of impregnation of the original fabric sheet with the chemical solution in two stages, namely before lamination and after lamination, due to which the size of the device increases and the original fabric sheet after lamination is impregnated with the chemical solution, a problem that occurs is that the amount of impregnation with the chemical solution varies between the surface of the laminated body and the center of the laminated body.

Additionally, according to the method disclosed in Patent Literature 2, there is a problem that because the original fabric sheet is folded up and compressed after being impregnated with the predetermined chemical solution, the predetermined chemical solution is wrung out from the original fabric sheet, and it may not be possible to manufacture a product having the desired amount of the predetermined chemicals.

Thus, the present invention has been achieved in view of the aforementioned problem, and an object thereof is to provide a method of manufacturing wet wipes, with which it is possible to manufacture wet wipes having the desired amount of a predetermined chemical solution while preventing an increase in the size of the device, a manufacturing apparatus therefor, and, and wet wipes.

According to a first aspect of the present invention, there is provided a method of manufacturing wet wipes including a laminated body of sheets impregnated with a predetermined chemical solution. method of manufacturing wet wipes includes a step of continuously conveying a plurality of sheets by a conveyor, a step of folding each of the sheets toward a conveyor non-contact surface side of the sheets, a step of impregnating each of the folded sheets with the predetermined chemical solution, from a conveyor contact surface side of the sheets a step of laminating each of the sheets impregnated with the predetermined chemical solution, and a step of cutting the laminated sheets.

According to a second aspect of the present invention, there is provided a manufacturing apparatus configured to manufacture wet wipes including a laminated body of sheets impregnated with a predetermined chemical solution. the device includes a conveyor device configured to continuously convey a plurality of sheets, a folding unit configured to fold each of the sheets toward a conveyor non-contact surface side of the sheets, an impregnating unit configured to impregnate each of the folded sheets with the predetermined chemical solution, from a conveyor contact surface side of the sheets, a lamination unit configured to laminate each of the sheets impregnated with the predetermined chemical solution, and a cutting unit configured to cut the laminated sheets.

According to a third aspect of the present invention, there is provided a Wet wipes including a laminated body of sheets impregnated with a predetermined chemical solution, the wet wipes comprising: protruding regions formed to protrude in a lamination direction of the laminated body along one direction of the laminated body due to folding of each sheet a plurality of times, wherein the protruding regions of each sheet that are vertically adjacent to each other in the lamination direction are arranged so as not to overlap in the lamination direction, and in the protruding regions, the sheets that are vertically adjacent to each other in the lamination direction are adhered and laminated through the predetermined chemical solution, and in the regions that are adjacent to the protruding regions, a gap is formed between the sheets that are vertically adjacent to each other in the lamination direction.

DESCRIPTION OF EMBODIMENTS

First Embodiment of the Present Invention

Figure 1:
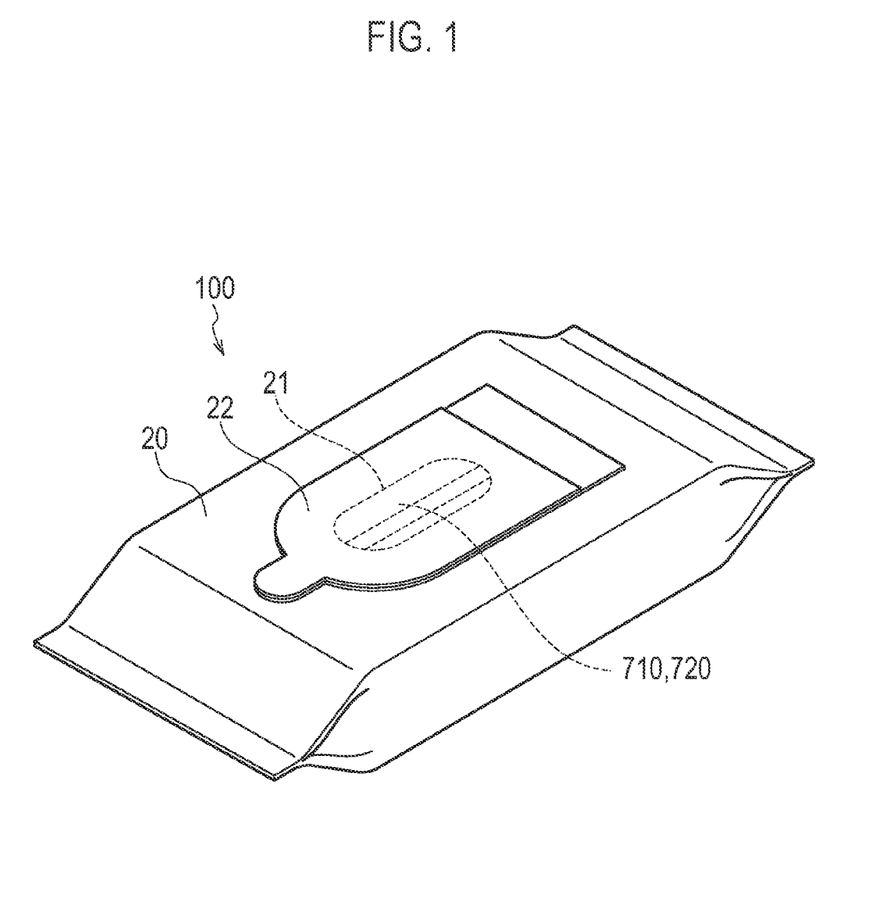
FIG. 1 is a perspective view of a package of wet wipes manufactured by a manufacturing apparatus according to a first embodiment of the present invention.
Figure 2:
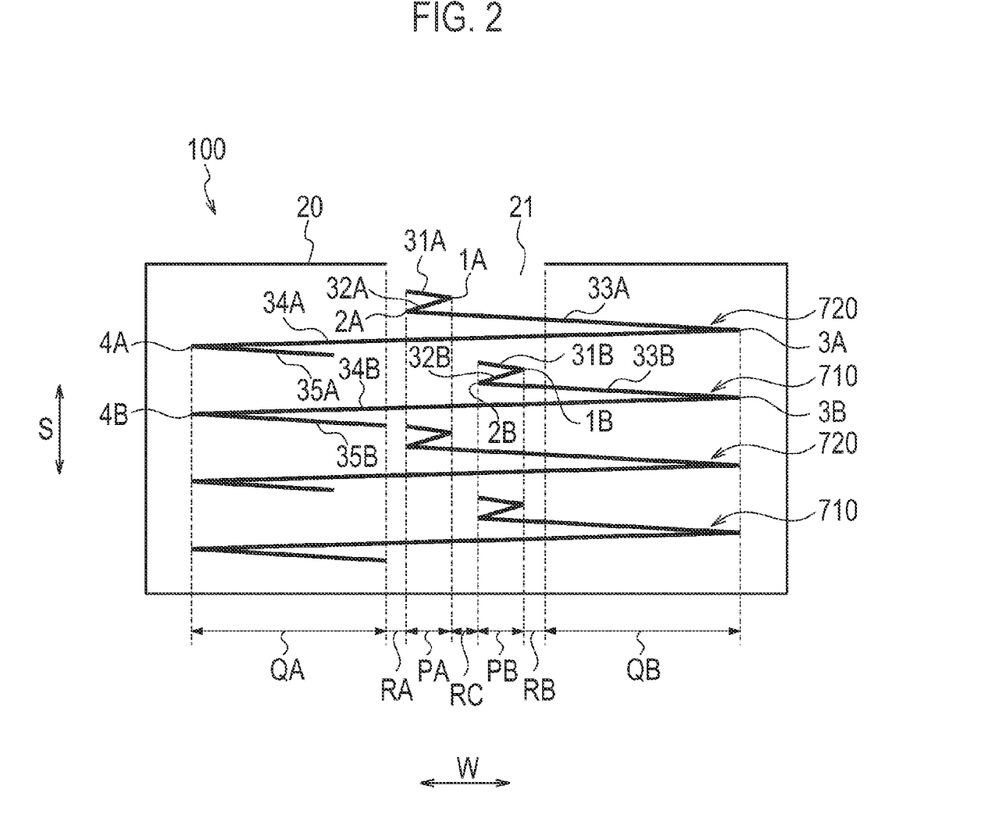
FIG. 2 is a diagram illustrating a state where wet wipes manufactured by the manufacturing apparatus according to the first embodiment of the present invention are stored inside the package.
Figure 3:
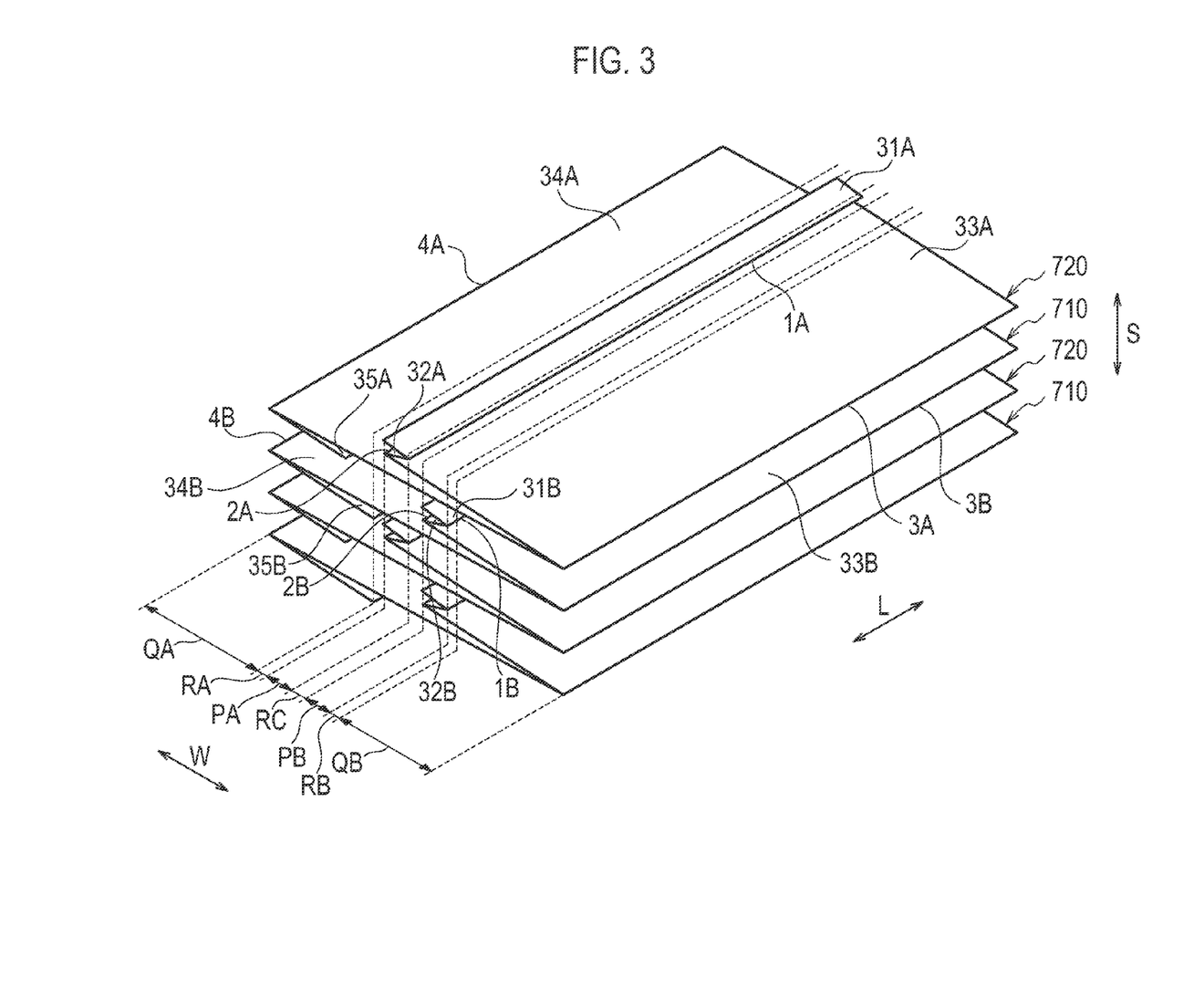
FIG. 3 is a diagram illustrating a state where the wet wipes manufactured by the manufacturing apparatus according to the first embodiment of the present invention are stored inside the package.

With reference to FIG. 1 through FIG. 3, wet wipes manufactured by a manufacturing apparatus 10 according to a first embodiment of the present invention will be described. The wet wipes include a laminated body of sheets 710 with a predetermined chemical solution and 720 impregnated with a predetermined chemical solution.

As illustrated in FIG. 1, a package 100 of the wet wipes includes a package main unit 20 having an opening 21, a label member 22 provided on an outer surface of the package main unit 20 and covering the opening 21, and a laminated body of the sheets 710 and 720 stored inside the package main unit 20.

As illustrated in FIG. 2 and FIG. 3, each of the sheets 710 and 720 is stored inside the package main unit 20 in a folded state.

As illustrated in FIG. 2 and FIG. 3, the sheet 720 includes a region 31A, region 32A, region 33A, region 34A, and region 35A, and the sheet 710 includes a region 31B, region 32B, region 33B, region 34B, and region 35B.

In the sheet 720, the region 31A and the region 32A are folded along the fold line 1A, the region 32A and the region 33A are folded along the fold line 2A, the region 33A and the region 34A are folded along the fold line 3A, and the region 34A and the region 35A are folded along the fold line 4A.

Similarly, in the sheet 710, the region 31B and the region 32B are folded along the fold line 1B, the region 32A and the region 33A are folded along the fold line 2B, the region 33A and the region 34A are folded along the fold line 3B, and the region 34A and the region 35A are folded along the fold line 4B.

It should be noted that in the sheet 720, the fold line 1A and the fold line 2A are provided between the fold line 3A and the fold line 4A in the other direction W, and in the sheet 710, the fold line 1B and the fold line 2B are provided between the fold line 3B and the fold line 4B in the other direction W of the laminated body.

That is, in the sheet 720, the region between the fold line 1A and the fold line 2A in the other direction W is a four-layered structure in which the region 31A, region 32A, region 33A, and region 34A are folded, and the other regions are two-layered structures in which the region 33A and the region 34A are folded.

Therefore, the region 31A and the region 32A protrude in the lamination direction S of the laminated body along one direction L of the laminated body.

That is, the region 31A and the region 32A configure a protruding region PA formed to protrude in the lamination direction S along one direction L in the laminated body due to folding along the fold line 1A and the fold line 2A.

Similarly, in the sheet 710, the region between the fold line 1B and the fold line 2B in the other direction W is a four-layered structure in which the region 31B, region 32B, region 33B, and region 34B are folded, and the other regions are two-layered structures in which the region 33B and the region 34B are folded.

Therefore, the region 31B and the region 32B protrude in the lamination direction S of the laminated body along one direction L of the laminated body.

That is, the region 31B and the region 32B configure a protruding region PB formed to protrude in the lamination direction S along the longitudinal direction L in the laminated body due to folding along the fold line 1B and the fold line 2B.

In the protruding region PA (or PB) of the sheets 710 and 720, the region 31A (or 31B) that includes one side edge of the sheet 720 (or 710), and the region 32A (or 32B) adjacent to the region 31A (or 31B) are folded along the fold line 1A (or 1B) in one direction L of the laminated body, and the region 32A (or 32B) as well as the region 33A (or 33B) adjacent to the region 32A (or 32B) are folded along the fold line 2A (or 2B) in one direction L of the laminated body. Furthermore, in the lamination direction S, the region between the fold line 1B and the fold line B (that is, the protruding region PA) in the widthwise direction W is arranged so as not to overlap the region between the fold line 1B and the fold line B (that is, the protruding region PB) in the other direction W.

Additionally, in the protruding regions PA and PB, the sheets 710 and 720 that are adjacent to each other in the lamination direction S are adhered and laminated through a predetermined chemical solution.

In regions RA, RB, and RC that are adjacent to the protruding regions PA and/or PB, a gap is formed between the sheets 710 and 720 that are adjacent to each other in the lamination direction S due to which the sheets are not adhered and laminated through a predetermined chemical solution.

Therefore, as the sheets 710 and 720 are not adhered with each other due to the gap formed between the sheets, when the protruding region PA of the sheet 720 is held and the sheet 720 is taken out, the sheet 720 is easily ripped off from the sheet 710 because of the gap that exists in the region RC of the sheet 710 that is positioned at the lower side of the sheet 720. It should be noted that in regions QA and QB outside the regions RA, RB, and RC in the widthwise direction W, sheets 710 and 720 that are adjacent to each other in the lamination direction S are adhered and laminated through a predetermined chemical solution. Because the sheets manufactured by the manufacturing apparatus 10 according to the first embodiment of the present invention do not have the aforementioned pop-up type form, even when the sheet 720 is taken out from the opening 21 of the package main unit 20, the sheet 710 does not protrude out from the opening 21 by being pulled out together.

That is, after taking out the sheet 720 by holding and pulling the region 31A and the region 32A (that is, the protruding region PA of the sheet 720) from the opening 21 of the package main unit 20, the user can take out the sheet 710 by holding and pulling the region 31B and the region 32B (that is, the protruding region PB of the sheet 710).

Hereinafter, with reference to FIG. 4, the method of manufacturing the wet wipes according to the present embodiment will be described in short.

Figure 4:
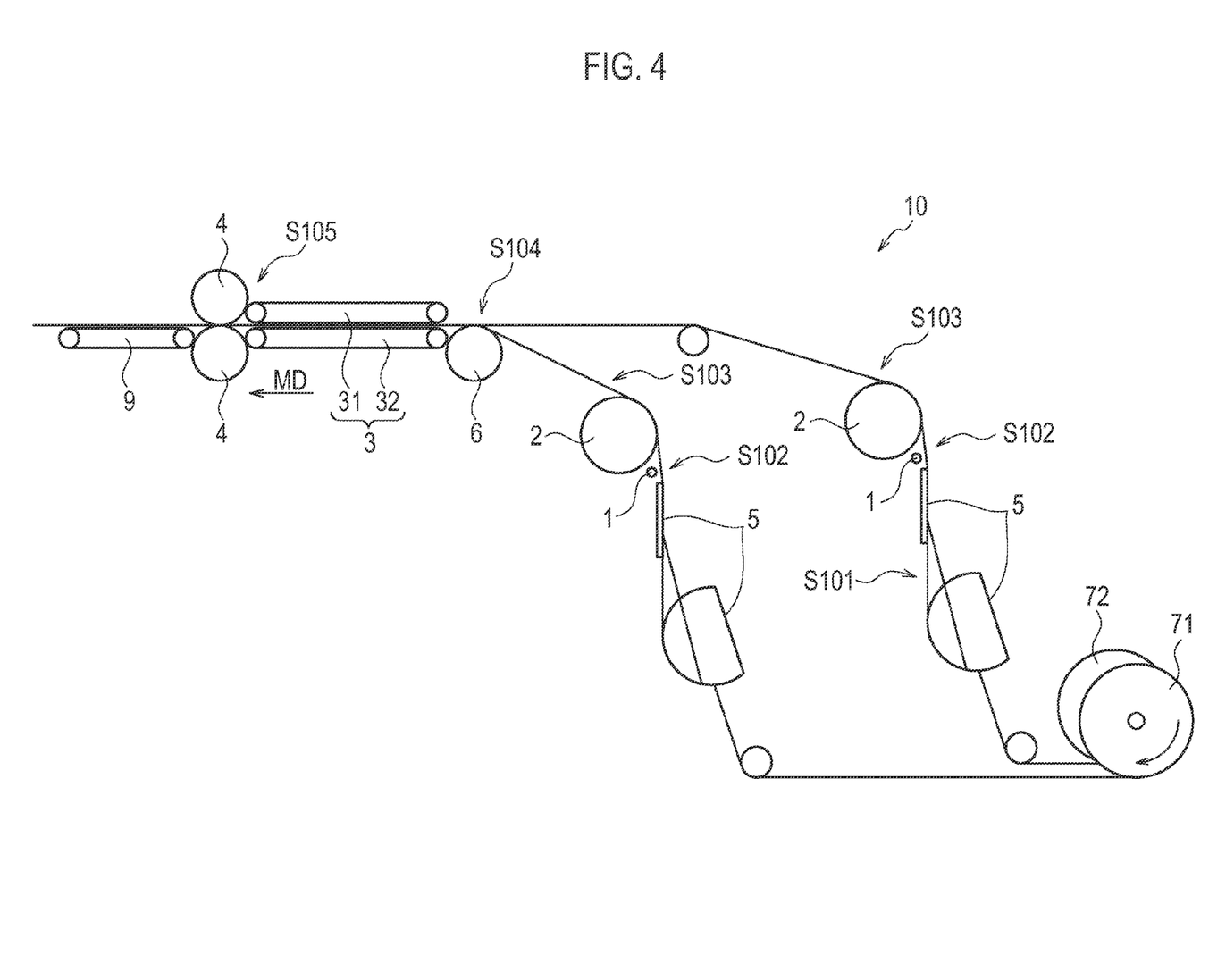
FIG. 4 is a schematic view of the manufacturing apparatus according to the first embodiment of the present invention.

As illustrated in FIG. 4, in step S101, a folding unit 5 folds each of the sheets 71 and 72 that are reeled out from a state of being wrapped in a roll, folds each of the sheets 71 and 72 to a conveyor non-contact surface side of the sheets in a way that it create a predetermined shape (specifically, the shape illustrated in FIG. 2 and FIG. 3).

For example, the sheets 71 and 72 have a basis weight of 25 to 100 g/m$^2$, and are made from fibers including hydrophilic fibers such as rayon, cotton, or pulp, and simple substances such as PET, PP, PE, and acryl, or from hydrophobic composite fibers having a core-clad structure or a side-by-side structure.

Furthermore, the sheets 71 and 72 are a nonwoven fabric that has been converted to sheets by the spunlace method, the air-laid method, or the direct spinning method, and must include hydrophilic fibers from the viewpoint of permeability of the predetermined chemical solution during impregnation with the predetermined chemical solution.

In step S102, an impregnating unit 1 impregnates each of the folded sheets 71 and 72 with a predetermined amount of the predetermined chemical solution, from the conveyor contact surface side of the sheets e (the side of conveyance roller).

In step S103, each of the sheets 71 and 72 that have been impregnated with the predetermined chemical solution is conveyed while being in contact with the surface of the conveyance roller 2.

In step S104, a lapping roller 6 laminates each of the sheets 71 and 72 that have been impregnated with the predetermined chemical solution.

Specifically, with the lapping roller 6, the sheet 72 that is in a state in which the surface that has been impregnated with the predetermined chemical solution faces the side at which the conveyor is in contact (lapping roller 6 side) is laminated on sheet 71 that is in a state in which the surface that has been impregnated with the predetermined chemical solution faces the side at which the conveyor is in contact (lapping roller 6 side), from the side at which the conveyor is not in contact.

In step S105, a cutting unit 4 cuts the sheets 71 and 72 conveyed via a conveyer belt 3 into sheets 710 and 720 of a predetermined size.

Following this, in a lamination step, after laminating only the predetermined number of the cut sheets 710 and 720, the laminated body was packaged by the package main unit 20 in a packaging step.

Hereinafter, with reference to FIG. 4 through FIG. 7, each function of the manufacturing apparatus 10 according to the present embodiment will be described.

As illustrated in FIG. 4, the manufacturing apparatus 10 is equipped with the folding unit 5, the impregnating unit 1, the conveyance roller 2, the lapping roller 6, conveyors 3 and 9, and a cutting unit 4. In the manufacturing apparatus 10, the conveyance roller 2 and the conveyors 3 and 9 constitute a conveyor configured to continuously convey a plurality of sheets 71 and 72.

The folding unit 5 is configured to fold each of the sheets 71 and 72 toward the conveyor non-contact surface side of the sheets. Specifically, the folding unit 5 is configured to fold each of the sheets 71 and 72 such that the sheets 71 and 72 take the shape illustrated in FIG. 2 and FIG. 3.

Specifically, the folding unit 5 is configured to fold the regions 31A, 32A, and 33A (or 31B, 32B, and 33B) including one side edge of the sheet 72 (or 71) toward the conveyor non-contact surface side of the sheet, along the fold line 3A (or 3B) in the conveyance direction MD, then fold the regions 31A and 32A (or 31B and 32B) including one side edge of the sheet 72 (or 71) toward the side at which the conveyor is not in contact, along the fold line 2A (or 2B) in the conveyance direction MD, and finally fold the region 31A (or 31B) including one side edge of the sheet 72 (or 71) toward the conveyor contact surface side of the sheets, along the fold line 1A (or 1B) in the conveyance direction MD.

Furthermore, the folding unit 5 is configured to fold the region 35A (or 35B) including the other side edge of the sheet 72 (or 71) toward the conveyor contact surface side of the sheets, along the fold line 4A (or 4B) in the conveyance direction MD.

The impregnating unit 1 is configured to impregnate each of the folded sheets 71 and 72 with the predetermined chemical solution, from the conveyor non-contact surface side of the sheets.

For example, the impregnating unit 1 may be configured to push out a predetermined amount of the predetermined chemical solution from a chemical tank by using a metering pump. As a result, the configuration is such that the predetermined amount of the predetermined chemical solution is discharged from the fine pores provided in the impregnating unit 1, and comes in contact with each of the sheets 71 and 72 because of which each of the sheets 71 and 72 are impregnated with the predetermined amount of the predetermined chemical solution.

Furthermore, the impregnating unit 1 may be configured such that the sheets 71 and 72 are impregnated with as much as the predetermined chemical solution, for example, 3.5 (3 to 4) times of the sheets 71 and 72, by weight.

It should be noted that the impregnating unit 1 can appropriately adjust the ratio of weight of the predetermined chemical solution used for impregnation with respect to the weight of sheets 71 and 72 (that is, the rate of impregnation).

The rate of impregnation necessary for the sheets 71 and 72 to stick to the surface of the conveyance roller 2, and for the sheet 72 to stick on the sheet 71 is 1.5 times or more when, for example, a 38 g/m$^2$-spunlace nonwoven cloth primarily containing rayon fibers is used for the sheets 71 and 72.

Furthermore, as a method of coating the predetermined chemical solution, the impregnating unit 1 may use a method of adhering the predetermined chemical solution that is in the form of liquid droplets or mist to the sheets 71 and 72. However, in view of the chemical solution impregnation efficiency and process contamination when the surface of the sheets 71 and 72 that is impregnated with the predetermined chemical solution is brought in contact with the surface of the conveyance roller 2, the aforementioned method is preferable.

The conveyance roller 2 is connected to a drive source, and is a drive roller rotating on its own and having a smooth surface.

Figure 5:
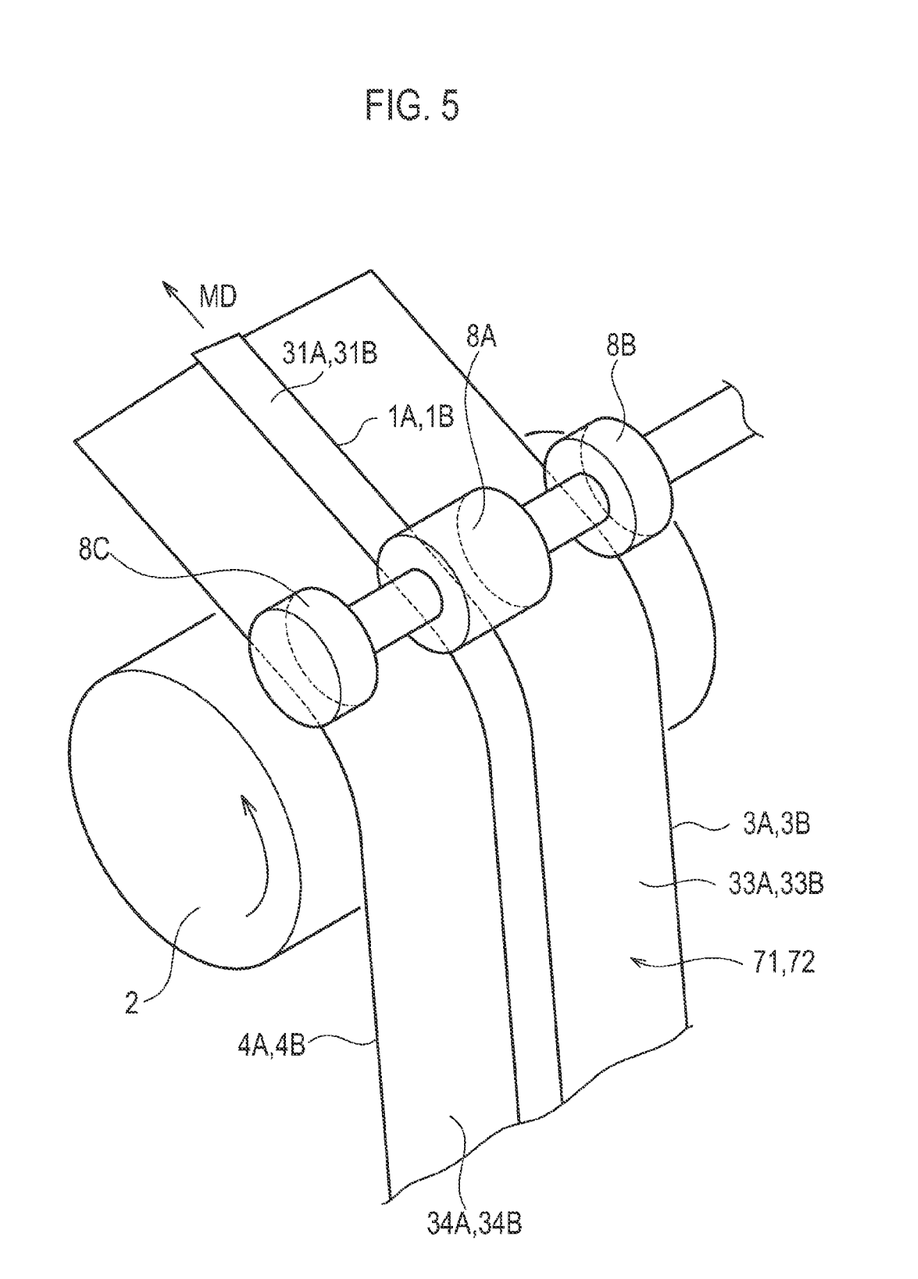
FIG. 5 is a diagram for explaining a holding roller of the manufacturing apparatus according to the first embodiment of the present invention.

As illustrated in FIG. 5, holding rollers 8A through 8C may be provided at the position opposite the conveyance roller 2.

The holding rollers 8A through 8C are configured to apply pressure to the locations folded by the folding unit 5 (locations corresponding to the fold lines 1A through 4A and locations corresponding to the fold lines 1B through 4B as illustrated in FIG. 2, hereinafter referred to as "folded location") in the sheets 71 and 72 that are impregnated with the predetermined chemical solution.

For example, the holding roller 8A is configured to apply pressure to the location corresponding to the fold lines 1A and 2A in the sheet 72, and the location corresponding to the fold lines 1B and 2B in the sheet 71.

Furthermore, the holding roller 8B is configured to apply pressure to the location corresponding to the fold line 3A in the sheet 72, and the location corresponding to the fold line 3B in the sheet 71.

Additionally, the holding roller 8C is configured to apply pressure to the location corresponding to the fold line 4A in the sheet 72, and the location corresponding to the fold line 4B in the sheet 71.

As a result, a crease can be made at the folded location because of which the conveyance of the sheets 71 and 72 can be stabilized.

On the surface of the holding rollers 8A through 8C, a convex portion may be formed at the position corresponding to the folded locations in the sheets 71 and 72. As a result, the oozing of the predetermined chemical solution with which the sheets 71 and 72 are impregnated due to the sheets being sandwiched by the holding rollers 8A through 8C and the conveyance roller 2 can be prevented.

Furthermore, dents may be interspersed on the surface of the holding rollers 8A through 8C. As a result, the effect of reduction in oozing of the predetermined chemical solution improves further.

The lapping roller 6 constitutes the lamination unit configured to laminate each of the sheets 71 and 72 impregnated with the predetermined chemical solution. Furthermore, the lapping roller 6 is a roller having a smooth surface, which is configured to convey each of the sheets 71 and 72 with a conveyance velocity that is substantially equivalent to that of the conveyance roller 2.

The conveyor 3 is configured to convey each of the sheets 71 and 72 with a conveyance velocity that is substantially equivalent to that of the conveyance roller 2.

Figure 6:
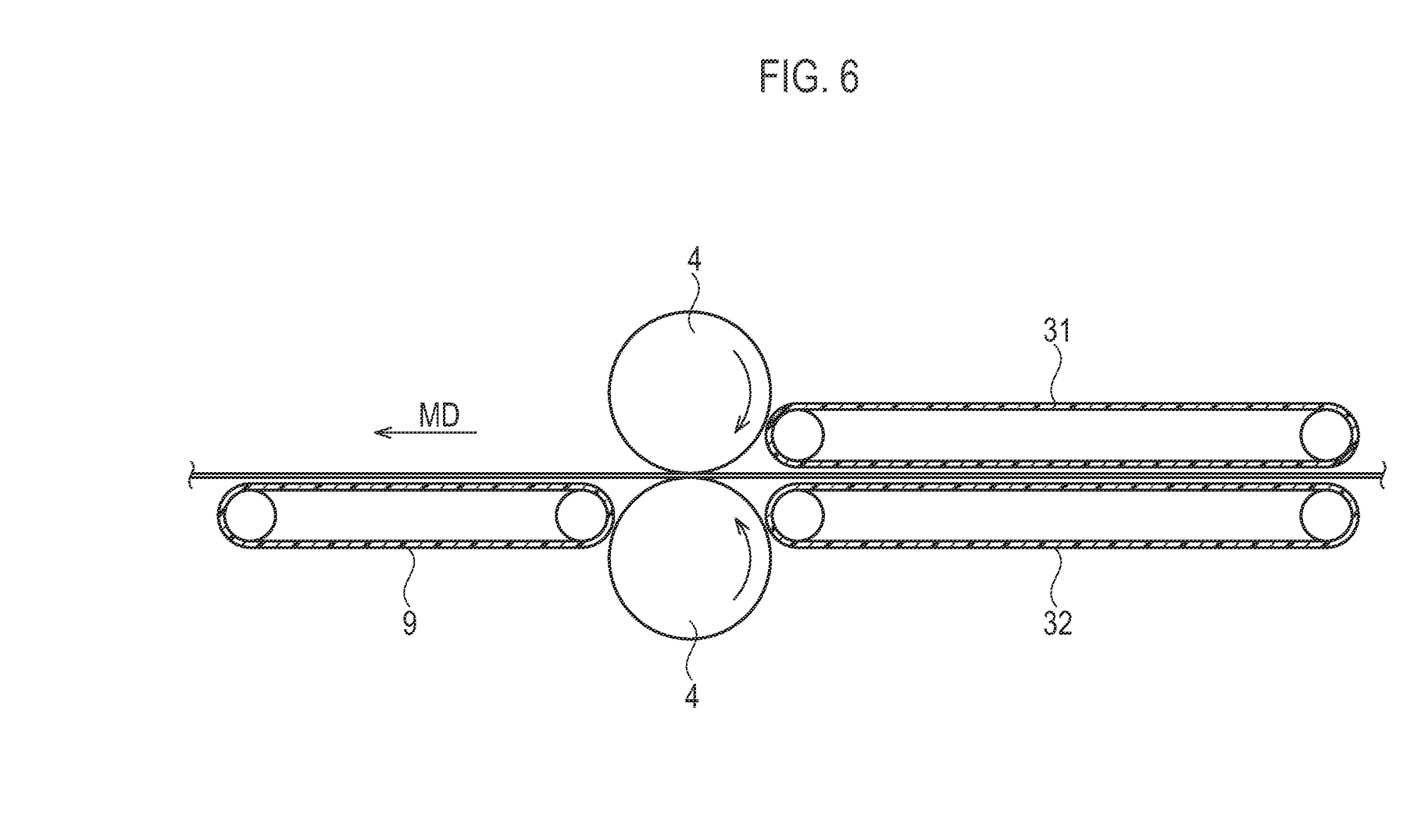
FIG. 6 is a diagram for explaining a conveyor of the manufacturing apparatus according to the first embodiment of the present invention.

For example, as illustrated in FIG. 6, the conveyor 3 may include an upper conveyor 31 and a lower conveyor 32. In such a case, a laminated body of the sheets 71 and 72 is conveyed while being sandwiched by the upper conveyor 31 and the lower conveyor 32 toward the cutting unit 4.

Figure 7:
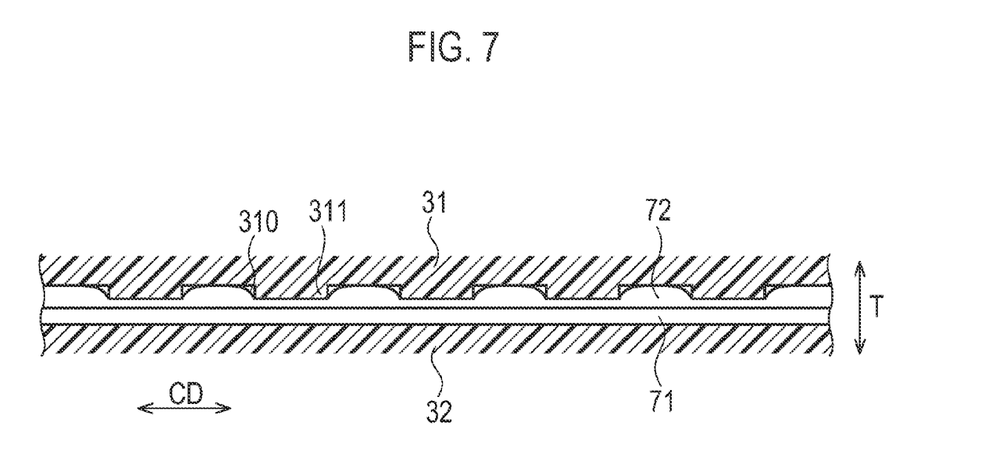
FIG. 7 is a diagram for explaining a conveyor of the manufacturing apparatus according to the first embodiment of the present invention.

FIG. 7 illustrates a cross-sectional view in the widthwise direction (crossing direction when the conveyance direction is considered as MD) of the laminated body of the sheets 71 and 72 sandwiched by the upper conveyor 31 and the lower conveyor 32.

As illustrated in FIG. 7, concave portions 310 and convex portions 311 may be formed alternately in the crossing direction CD and continuously in the conveyance direction MD (direction on one side of the laminated body of the sheets 71 and 72), at the side, at which the sheet 72 is in contact, of the upper conveyor 31.

In such a case, concave portions and convex portions need not necessarily be formed at the side, at which the sheet 71 is in contact, of the lower conveyor 32, that is, the side, at which the sheet 71 is in contact, of the lower conveyor 32 may be formed in a smooth manner.

As a result, in comparison to the sheet 71, the sheet 72 is conveyed in a state such that the sheet 72 is pressed in the thickness direction T in the region that is in contact with the convex portions 311 of the upper conveyor 31 rather than the region that is in contact with the concave portions 310 of the upper conveyor 31.

Furthermore, the concave portions 310 and the convex portions 311 formed on the surface of the upper conveyor 31 need not necessarily be parallel in the widthwise direction of the sheet 72.

The cutting unit 4 is configured to cut the laminated body of the sheets 71 and 72. For example, the cutting unit 4 includes a cutter roll having a cutting blade on the surface and an anvil roll having a smooth surface.

Furthermore, same as the conveyor 3, the conveyor 9 may include an upper conveyor and a lower conveyor. In such a case, the laminated body of the sheets 710 and 720 is conveyed while being sandwiched by the upper conveyor and the lower conveyor.

As a result, the transferability, to the conveyor 9, of the laminated body of the sheets 710 and 720 after being cut by the cutting unit 4, and the conveyance stability thereof can be improved. Furthermore, same as the upper conveyor 31 of the conveyor 3, concave portions and convex portions may be formed in the upper conveyor.

The conveyance velocity of the conveyor 9 is approximately 3% faster than the conveyance velocity of the conveyor 3 and the cutting unit 4.

According to the manufacturing method and the manufacturing apparatus 10 of the present embodiment, because the sheets 71 and 72 can be conveyed without wringing out or sucking in the predetermined chemical solution with which the sheets 71 and 72 are impregnated, wet wipes in which a predetermined amount of the predetermined chemical solution is retained can be manufactured.

Furthermore, according to the manufacturing method and the manufacturing apparatus 10 of the present embodiment, as compared to the conventional pop-up type wet wipes, even when the amount of impregnation with the predetermined chemical solution is increased, wet wipes that can be taken out one sheet at a time can be manufactured easily.

Generally, because the folding unit 5 is configured to fold up the sheets 71 and 72 into the required shape via a plurality of folding plates, when the sheets 71 and 72 impregnated with the predetermined chemical solution attempt to pass, the adhesion (that is, the conveyance resistance) between the folding plates and the sheets 71 and 72 increases due to the predetermined chemical solution, because of which the sheets 71 and 72 are conveyed while the predetermined chemical solution is being wrung out by the folding plates.

Although this tendency becomes remarkable when the amount of impregnation of the sheets 71 and 72 with the predetermined chemical solution increases, according to the manufacturing method and the manufacturing apparatus 10 of the present embodiment, the impregnating unit 1 is arranged after the point to start folding by the folding unit 5, because of which the conveyance resistance by each of the folding plates of the folding unit 5 is reduced. Furthermore, as a result of the aforementioned arrangement, the mixing of impurities from the folding unit 5 can be reduced.

Furthermore, according to the manufacturing method and the manufacturing apparatus 10 of the present embodiment, by bringing that surface impregnated with the predetermined chemical solution, of the sheets 71 and 72, in contact with the surface of the conveyance roller 2, which has been impregnated with the predetermined chemical solution, the surface of the conveyance roller 2 and the sheets 71 and 72 adhere because of the water film of the predetermined chemical solution, and the conveyance force of the sheets 71 and 72, which have been impregnated with the predetermined chemical solution, towards the conveyance roller 2 can be improved.

At this time, the length (included angle) of the time period of contact between the sheets 71 and 72 impregnated with the predetermined chemical solution and the conveyance roller 2 is adjusted appropriately with the amount of impregnation of the sheets 71 and 72 with the predetermined chemical solution.

In addition to the conveyor roller 2, the lapping roller 6 and the conveyor 3 also exhibit conveyance force due to water-film adhesion, and therefore, nip roller conveyance, suction conveyance, and the like need not be provided for the sheets 71 and 72 impregnated with the predetermined chemical solution. As a result, the sheets 71 and 72 can be conveyed without wringing out the predetermined chemical solution.

Furthermore, on the conveyance roller 2, by applying pressure to the folded locations of the sheets 71 and 72 with the holding roller 8 that are provided with convex portions on the surface, the folded locations can be flattened, and the adhesion during subsequent overlapping of the sheets 71 and 72 can be improved.

Furthermore, when a plurality of the sheets 71 and 72 impregnated with the predetermined chemical solution are overlapped and conveyed, if the lower surface of the sheet 72 overlapping the top of the sheet 71 is the surface impregnated with the predetermined chemical solution, the sheets 71 and 72 can be conveyed without any deviation, while maintaining the state of adhesion of the sheets 71 and 72.

At this time, if the sheets overlap in such a way that the surface that is impregnated with the predetermined chemical solution of the sheet 71 matches the surface that is impregnated with the predetermined chemical solution of the sheet 71, the conveyance stability during manufacturing improves further, however, when the wet wipes are used after manufacturing, the peelability of the sheets deteriorates resulting in a decline in the ease of extracting the sheets, which is not preferable.

Conversely, if the surface that is impregnated with the predetermined chemical solution of the sheet 72 does not match the surface that is impregnated with the predetermined chemical solution of the sheet 71, then not just the ease of conveying the sheets but the ease of extracting the sheets deteriorates, which is not preferable.

Furthermore, according to the manufacturing method and the manufacturing apparatus 10 of the present embodiment, the conveyance velocity of the conveyor 9 is faster than the conveyance velocity of the cutting unit 4.

Therefore, until being cut by the cutting unit 4, the laminated body of the sheets 71 and 72 is maintained at the conveyance velocity of the conveyor 3, and after cutting, the laminated body is conveyed by the conveyance velocity of the conveyor 9.

In order to convey the laminated body of sheets 71 and 72 to the cutting unit 4 in a stable manner, without any meandering, for example, it is preferred to convey the laminated body of the plurality of sheets 71 and 72 while sandwiching the same between the upper conveyor 31 and the lower conveyor 32.

However, at this time, if the laminated body of the sheets 71 and 72 is compressed excessively from the top and the bottom, the predetermined chemical solution may ooze out, and therefore, by forming at least one surface of the upper conveyor 31 and the lower conveyor 32 in such a shape that the concave portions 310 and the convex portions 311 that are repeated alternately in the widthwise direction are arranged in continuation in the longitudinal direction, the laminated body of the sheets 71 and 72 can be conveyed while being retained by the convex portions 311 interspersed in the widthwise direction, and with the space being retained by the concave portions 310.

Therefore, while the conveyance stability during manufacturing is improved, between the tissue papers can also be peeled off easily during the use of the wet wipes. Additionally, after the laminated body of the sheets 71 and 72 is cut and the plurality of sheets are laminated to form a laminated body of sheets that is the final product, a space is formed between the sheets unless excessive compression is performed after generating the laminated body of sheets as the final product, and therefore, the same effect is exhibited even during usage.

Furthermore, when one surface of the upper conveyor 31 and the lower conveyor 32 is smooth, the sheets 71 and 72 can be conveyed by the adhesion resulting from the water film formed between the surface thereof and the sheets 71 and 72, and wringing out of the predetermined chemical solution due to the compression of the sheets 71 and 72 can be prevented.

Thus, the present invention has been explained in detail by using the above-described embodiments; however, it is obvious that for persons skilled in the art, the present invention is not limited to the embodiments explained herein. The present invention can be implemented as corrected and modified modes without departing from the gist and the scope of the present invention defined by the claims. Therefore, the description of the specification is intended for explaining the example only and does not impose any limited meaning to the present invention.

In addition, the entire content of Japanese Patent Application No. 2010-091724 (filed on Apr. 12, 2010) is incorporated in the present specification by reference.

INDUSTRIAL APPLICABILITY

As described above, according to the present invention, it is possible to provide a method of manufacturing wet wipes with which it is possible to manufacture wet wipes having the desired amount of a predetermined chemical solution while preventing an increase in the size of the device, a manufacturing apparatus therefor, and wet wipes.

REFERENCE SIGNS LIST

10 . . . Manufacturing apparatus
1 . . . Impregnating unit
2 . . . Conveyance roller
3, 9 . . . Conveyor
4 . . . Cutting unit
5 . . . Folding unit
6 . . . Lapping roller
71, 72 . . . Sheet
8A, 8B, 8C . . . Holding roller

The invention claimed is:

1. A manufacturing apparatus configured to manufacture wet wipes including a laminated body of sheets impregnated with a predetermined chemical solution, the apparatus comprising:
   a conveyor device configured to continuously convey a plurality of sheets, each of the sheets having a first side configured to be in contact with a surface of the conveyor device and a second side configured to be not in contact with the surface of the conveyor device;
   a folding unit configured to fold each of the sheets toward the second side of the sheet;
   an impregnating unit configured to impregnate each of the folded sheets with the predetermined chemical solution at a predetermined rate of impregnation from the first side of the sheet;
   a lamination unit configured to laminate together the sheets that have been folded and impregnated with the predetermined chemical solution; and
   a cutting unit configured to cut the laminated sheets,
   wherein the predetermined rate of impregnation is more than a rate of impregnation necessary for the sheets to stick to the surface of the conveyor device and for one of the sheets to stick onto another of the sheets.

2. The manufacturing apparatus according to claim 1, further comprising:
an upper conveyor belt and a lower conveyor belt configured to continuously convey the laminated sheets in a conveyance direction while sandwiching the laminated sheets between the upper conveyor belt and the lower conveyor belt, wherein
the upper conveyor belt and the lower conveyor belt are arranged in a zone between the lamination unit and the cutting unit,
the lower conveyor belt has an upper side configured to contact with a lowermost sheet among the laminated sheets,
the upper conveyor belt has a lower side configured to contact with an uppermost sheet among the laminated sheets, and
at least one of the lower side of the upper conveyor belt and the upper side of the lower conveyor belt includes concave and convex portions which are alternately arranged in a crossing direction crossing the conveyance direction and continuously extend in the conveyance direction.

3. The manufacturing apparatus according to claim 2, wherein
the lower side of the upper conveyor belt includes said concave and convex portions, and
the upper side of the lower conveyor belt is smooth.

4. The manufacturing apparatus according to claim 1, wherein
the conveyor device comprises a conveyance roller and a holding roller configured to sandwich the sheets that have been folded and impregnated with the predetermined chemical solution,
the conveyance roller and the holding roller are arranged in a zone between the impregnating unit and the lamination unit, and
the holding roller has a surface including convex portions.

5. The manufacturing apparatus according to claim 1, wherein
the folding unit is configured to fold each of the sheets by:
folding a region including one side edge of the sheet, along a first fold line in a conveyance direction, toward the second side of the sheet;
then, folding the region including said one side edge of the sheet, along a second fold line in the conveyance direction, toward the second side of the sheet; and
then, folding the region including said one side edge of the sheet, along a third fold line in the conveyance direction, toward the second side of the sheet.

6. The manufacturing apparatus according to claim 5, wherein the folding unit is further configured to fold each of the sheets by
folding another region including another side edge of the sheet along a fourth fold line in the conveyance direction, toward the first side of the sheet,
wherein the side edges of the sheet are opposite to each other in a cross direction crossing the conveyance direction.

* * * * *